United States Patent [19]

Agarwal

[11] Patent Number: 4,560,815

[45] Date of Patent: Dec. 24, 1985

[54] AUTOMATED CATALYST REGENERATION IN A REACTOR

[75] Inventor: Suresh C. Agarwal, Euclid, Ohio

[73] Assignee: The Babcock & Wilcox Company, New Orleans, La.

[21] Appl. No.: 550,440

[22] Filed: Jan. 26, 1984

Related U.S. Application Data

[62] Division of Ser. No. 488,282, Apr. 25, 1983.

[51] Int. Cl.$^4$ .................................................. C07C 5/03
[52] U.S. Cl. ............................... 585/259; 208/DIG. 1
[58] Field of Search ................... 585/259; 208/DIG. 1

[56] References Cited

U.S. PATENT DOCUMENTS 4,236,219  11/1980  Killebrew et al. ................... 585/259
4,367,354  1/1983   Dibiano ............................... 585/259

FOREIGN PATENT DOCUMENTS 646408  11/1950  United Kingdom ................. 585/259
865299  4/1961   United Kingdom ................. 585/259

*Primary Examiner*—Curtis R. Davis
*Attorney, Agent, or Firm*—Vytas R. Matas; Robert J. Edwards

[57] ABSTRACT

A technique, including an apparatus, for automatically regenerating a catalyst used in a process for obtaining a product in an exit stream from a raw material in a feed stream of a reactor, comprises determining the concentration of raw material in the feed and exit stream and obtaining a value for the catalyst selectivity as a function of the difference between the concentrations. When a selected selectivity is reached, which is indicative of the need for the catalyst to be regenerated, regenerator equipment is activated for regenerating the catalyst in the reactor. To continue the process, the feed stream is transferred to an auxiliary reactor during regeneration of the primary reactor, which contains regenerated or fresh catalyst. When used in reactors for the hydrogenation of acetylene to ethylene, the concentration of hydrogen in the feed stream is also calculated with the selectivity equaling the concentration of hydrogen divided by the difference in concentrations for the acetylene in the feed and exit streams respectively.

4 Claims, 6 Drawing Figures

AUTOMATED CATALYST REGENERATION IN A REACTOR

This is a division of application Ser. No. 488,282, filed Apr. 25, 1983 Pending.

FIELD AND BACKGROUND OF THE INVENTION

The present invention relates in general to catalyst reactors and in particular to a new and useful method and apparatus of automatically regenerating a catalyst.

In many chemical, petrochemical and synthetic fuel manufacturing processes a raw material feed stream is passed over a catalyst in a reactor to either produce a desired product or remove certain impurities. The state of the catalyst is of prime importance to these operations because economic operation of a reactor and consequently the plant, is very much affected by the catalyst state. Product conversion, yield and operating temperature are dependent upon the selectivity of the catalyst.

A catalyst's selectivity decays with time because of a number of factors such as presence of impurities and their concentration in the feed stream, types of by-products from side reactions, duration of reactor operation, etc. For example in the selective hydrogenation of acetylene in an ethylene rich stream green oil, polymerization of green oil on the catalyst surface, etc. occurrs. These are deposited on the catalyst surface, thus reducing the surface area available for the reaction. Hence, acetylene hydrogenation to ethylene is reduced. The condition may also lead to a product which is off specification. Therefore, after operating a reactor with fresh or regenerated catalyst for some time, the catalyst is either regenerated by passing steam through the reactor or replaced by new catalyst whichever may be the case depending on a specific situation.

The state of the art for control of the selective hydrogenation of acetylene into ethylene in the ethylene rich stream is well documented in the following patents:
1. U.S. Pat. No. 2,802,889; Frevel et al
2. U.S. Pat. No. 2,814,653; Hogan et al
3. U.S. Pat. No. 3,113,980; Robinson et al
4. U.S. Pat. No. 3,153,679; Rottmayr
5. U.S. Pat. No. 3,471,582; Lupfer
6. U.S. Pat. No. 3,656,911; Hobbs
7. U.S. Pat. No. 3,972,804; McLaughlin et al
8. U.S. Pat. No. 4,236,219; Killebrew et al
9. U.S. Pat. No. 4,241,230; Drinkard
10. U.S. Pat. No. 4,249,907; Callejas These patents only teach the techniques for the temperature control of reactors. They do not provide for any indication of the current state of the catalyst. Consequently, any or all of the following situations may occur:

1. As catalyst selectivity decreases, less and less acetylene will be hydrogenated into ethylene. Thus, the probability for occurrence of product off-specification increases and ultimately may occur, thus resulting in loss of production.

2. The operator may increase operating temperature of the reactor to compensate for decline in catalyst selectivity on the basis of information from the manufacturer of the catalyst and acetylene concentration in the reactor exit stream. This presents a situation where an operator may be unable to discriminate among the causes for occurrences of more than normal acetylene concentration in the exit stream. This may be a result of several possible conditions, for example, sudden drop in feed temperature, sudden breakthrough of acetylene in cracking furnaces, malfunctioning of intermediate unit operations or their associated components, malfunctioning/failure of instruments, etc.

3. Increase in operating temperature of the reactor results in increasing energy consumption in the feed preheater, thus increasing coolant use in the inter catalyst bed cooler, and increases ethylene hydrogenation to ethane.

Moreover, in the current state of the art industrial practice, catalyst is regenerated either after occurrence of a severe product off specification or it has been scheduled by maintenance personnel on the reactor, on the basis of an elapsed period of operation or during plant shutdown. The same is applicable to catalyst change. Therefore, the reactor is normally operated with catalyst for a period longer than the recommended period between two successive regenerations and replacement by fresh catalyst. Therefore, one or more of the aforementioned three conditions may occur, or worse yet, the catalyst may be poisoned. The recommended period of operation between two successive catalyst regeneration is about 18 months. Continued operation without regeneration may poison the catalyst completely, thus reducing its life (normally about 5 years) and may require new catalyst.

SUMMARY OF THE INVENTION

The present invention is drawn to a method and apparatus for the automatic regeneration of catalyst in a reactor which is based on a value of the catalyst selectivity.

According to the invention, catalyst is regenerated in a timely fashion. This is important in view of the high cost of catalyst and the possibility of poisoning the catalyst beyond the point where it can be regenerated.

The invention also relates to an apparatus and method for the automatic regeneration of catalyst in a reactor wherein selective hydrogenation of specific unsaturated hydrocarbon is conducted for its removal from an olefin rich stream.

According to another feature of the invention, a standby reactor is available for the automatic regeneration of catalyst in a primary reactor. The invention can operate regardless of the type of reactor or catalyst except for the fluidized bed type of reactor.

Accordingly, an object of the present invention is to provide an apparatus for the automatic regeneration of catalyst used in a process for obtaining a product in an exit stream of a reactor, from a raw material in a feed stream of the reactor, the reactor having regeneration means activatable to regenerate the catalyst, comprising, first sensor means operatively connected to the feed stream for sensing a concentration of raw material in the feed stream, second sensor means operatively connected to the exit stream for sensing a concentration of raw material in the exit stream and a control system connected to the first and second sensor means for calculating a value for selectivity of the catalyst as a function of raw material concentration in the feed and exit streams, and for generating a control signal when the calculated selectivity value approaches a selected selectivity value which indicates the catalyst should be regenerated, the control system connected to the regeneration means for activating the regeneration means to regenerate the catalyst.

A further object of the invention is to provide such an apparatus which includes an auxiliary reactor having fresh or regenerated catalyst used in the process, the auxiliary reactor connected to the feed and exit streams over valves which are connected to and controlled by the control system to transfer the feed stream to the auxiliary reactor when the first mentioned reactor is undergoing regeneration of its catalyst.

A still further object of the invention is to provide such an apparatus wherein the process is the selective hydrogenation of a specific unsaturated hydrocarbon forming the raw material, for its removal from an olefin rich stream, the first and second sensor means operable to sense a concentration of the hydrocarbon in the feed and exit streams respectively with the first sensor means also being operable to sense a concentration of hydrogen in the feed stream, the control system including calculator means for calculating the selectivity of the catalyst according to the relationship $C_{H1}/(C_{A1}-C_{A2})$, wherein $C_{H1}$ is the concentation of hydrogen in the feed stream, $C_{A1}$ is the concentration of hydrocarbon in the feed stream and $C_{A2}$ is the concentration of hydrocarbon in the exit stream.

Another object of the invention is to provide a method of regenerating catalyst in a process for obtaining a product in an exit stream from a raw material in a feed stream, comprising sensing the concentration of raw material in the feed stream, sensing the concentration of raw material in the exit stream and determining the selectivity of the catalyst for the specific process as a function of the difference between the feed stream concentration and the exit stream concentration for the raw material.

Another object of the invention is to provide a method of regenerating a catalyst comprising providing an auxiliary reactor connected in parallel to a main reactor, to which the process is transferred during regeneration of catalyst in the primary reactor.

Another object of the invention is to provide a method of regenerating catalyst in an automatic manner using a NETWORK 90 system available from the Bailey Meter Company.

Another object of the invention is to provide an apparatus for automatically regenerating catalyst which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
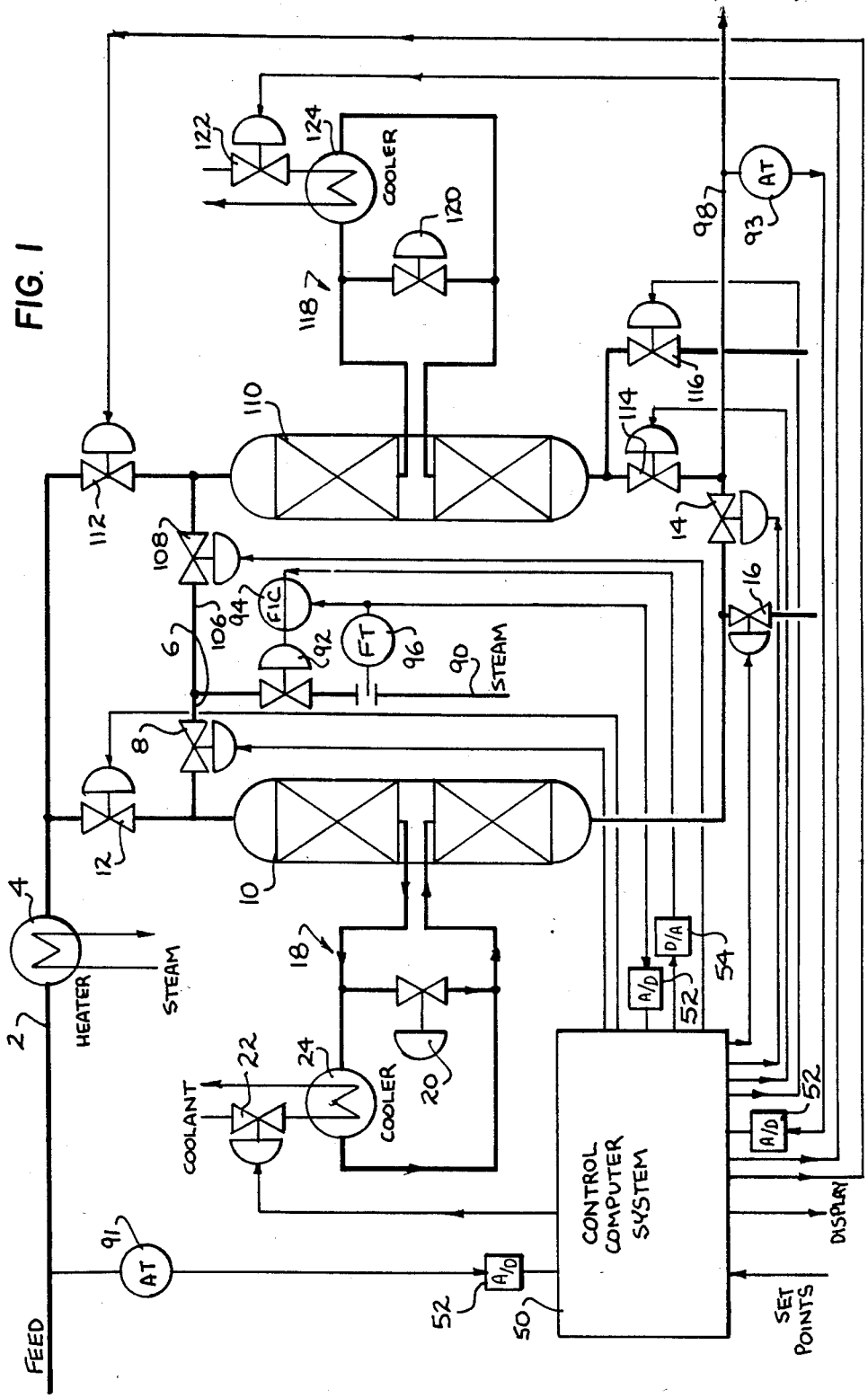
FIG. 1 is a schematic representation of an automatic catalyst regeneration system showing dual reactors with control and sensing elements.

Referring to the drawings in particular, the invention embodied therein, in FIG. 1, comprises an apparatus for automatically regenerating a catalyst in one of two reactors 10 and 110 which are of substantially identical design.

The reactor 10 is used as a primary reactor in a process for obtaining a product from a raw material using a catalyst, with the other reactor 110 being utilized as an auxiliary reactor during the period when the catalyst in the primary reactor is being regenerated.

The specific example illustated involves a process for the selective hydrogenation of acetylene to ethylene. The invention is suitable however, in the regeneration of catalysts in other processes.

As shown in FIG. 1, the feed stream containing ethylene, acetylene and hydrogen is provided over a feed line 2, past a heater 4 which, for example, uses steam and to inlet valve 12 at the inlet of primary reactor 10. Since the reactors 10 and 110 are substantially identical, corresponding parts in the two reactor systems will be designated with the same numerals except that numerals associated with the auxiliary reactor 110 are increased by 100.

A steam line 6 is connected to the inlet of reactor 10 and includes a regenerator valve 8. Line 6 is connected to a steam source 90 over a main steam valve 92 controlled by a FIC controller 94 which reacts to a computer control signal as well as a flow transmitter 96. With valves 8 and 92 open, steam is provided to the catalyst in reactor 10, to regenerate the catalyst.

In normal operation of reactor 10 for producing acetylene, however, at least valve 8 is closed. A line connects the outlet of reactor 10 to an outlet valve 14. A drain valve 16 is connected to a drain line upstream of outlet valve 14 for draining waste products of the regeneration cycle.

An exit line 98 is connected to the outlet valve 14 of reactor 10 as well as the outlet valve 114 of reactor 110.

Each of the reactors consists of two reactor beds separated by an intermediate cooling bed. The cooling bed of reactor 10 is connected to a cooling circuit 18 having a bypass valve 20 for regulating the temperature in reactor 10. Coolant is supplied to a heat exchanger 24 over a coolant valve 22. An identical cooling circuit 118 is provided for auxiliary reactor 110.

A chromatograph 91 measures the concentration of acetylene and hydrogen in the feed stream of feed line 2 and a second chromatograph 93 measures the concentration of acetylene in the exit stream of exit line 98.

Chromatographs 91 and 93 may be replaced by any suitable sensor for sensing raw material concentration in the feed and exit lines.

All sensors are connected to the computer system over analog to digital converters 52. The steam valve controller 94 is connected over a digital analog converter 54, to computer system 50.

The instrumentation and control schemes for reactors 10 and 110 are utilized for modulating the systems, as well as startup and shutdown operations. Specific details on the operation of the separate systems is known in the art and demonstrated in the above-identified patents.

In accordance with the invention, primary reactor 10 is initially used for the selective hydrogenation process while reactor 110 contains regenerated or fresh catalyst that is available for subsequent use.

In this state of the apparatus, valves 12, 22 and 14 are open while valves 8 and 16 are closed. All of the corresponding valves, 108, 112, 114, 116, and 122, in the auxiliary reactor system, are closed. Valve 20 is active for temperature control purposes in the selective hydrogenation process. While valve 120 is inactive. Valve 92 is closed since it is used for modulating control during the regeneration process.

As will become apparent hereinunder, the key features of the inventive control structure and method are:
1. The estimation of catalyst selectivity;
2. The detection of catalyst selectivity below a normal required level;
3. Transfer of selective hydrogenation to the auxiliary reactor 110 upon detection of an unsatisfactory condition in the catalyst of primary reactor 10;
4. The subsequent regeneration of catalyst in reactor 10;
5. The bringing of primary reactor 10 to a ready state for the takeover of selective hydrogenation from reactor 110; and
6. Catalyst status accounting.

In accordance with the invention, a measurement of catalyst selectivity toward acetylene hydrogenation to ethylene is obtained by the algorithm:

$$S = C_{H1}/(C_{A1} - C_{A2})$$

where;
 $S$ = Selectivity of the catalyst
 $C_{A1}$ = Acetylene concentration in the feed stream
 $C_{A2}$ = Acetylene concentration in the exit stream
 $C_{H1}$ = Hydrogen concentration in the feed stream.

Figure 2:
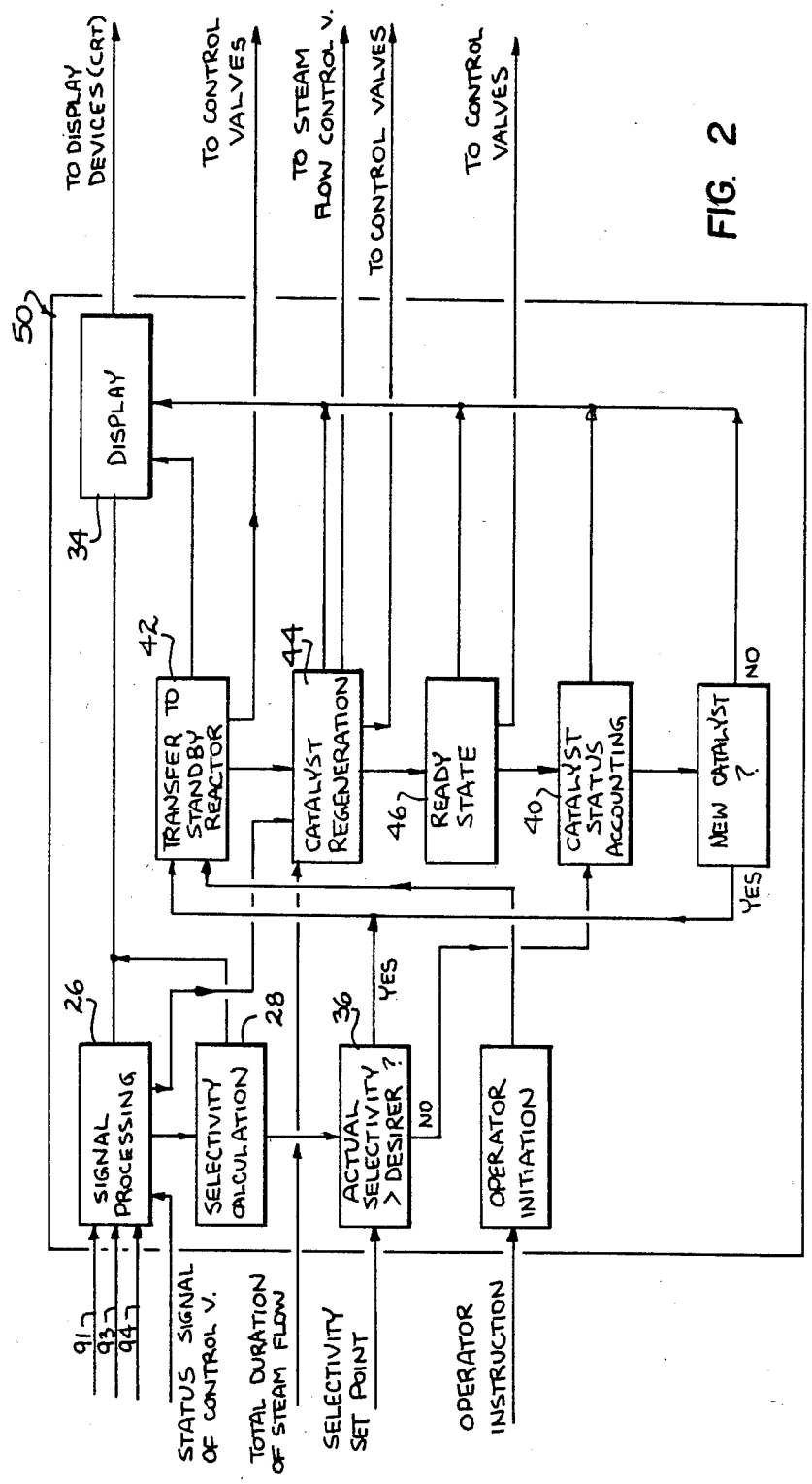
FIG. 2 is a block diagram showing additional details of a central computer system used in accordance with the invention.

Acetylene and hydrogen concentration in the feed stream are provided by chromatograph 91. Acetylene concentration in the exit stream is provided by chromatograph 93. These signals are provided to the control computer system 50 where they are processed for noise and converted to engineering units in a signal processing block 26 shown in FIG. 2. This is based on known principles of signal processing.

Figure 3:
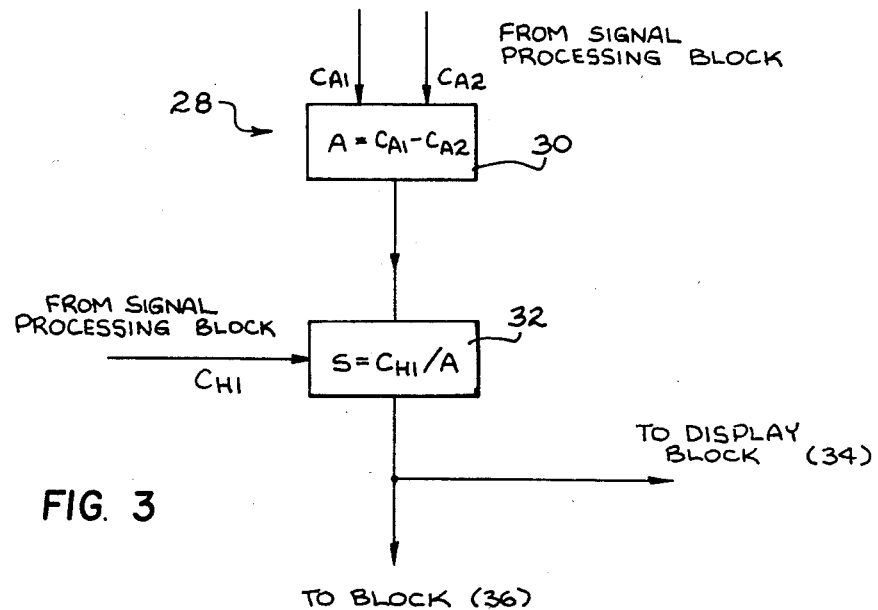
FIG. 3 is a block diagram showing additional details of a unit found in the control computer for establishing an actual catalyst selectivity value.

The signals are then provided to selectivity calculation block 28 where the selectivity calculation is performed according to the algorithm set forth above. Details of block 28 are shown in FIG. 3 where a subtraction unit 30 takes the difference between feed and exit stream acetylene concentrations which value forms the divisor of the hydrogen concentration in a division unit 32. The output of unit 32 is sent to a display block 34 as well as a desired selectivity block 36.

The current selectivity value for the catalyst is thus displayed to the operator over display block 34 which is of known design.

Figure 4:
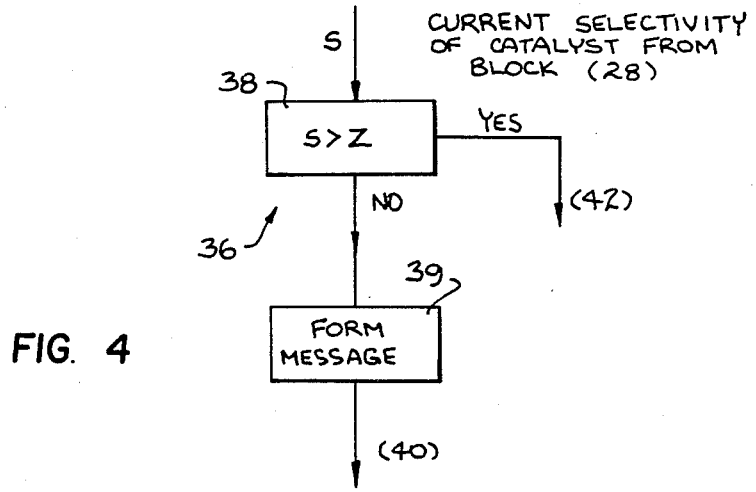
FIG. 4 is a block diagram showing additional details of a unit in the sub-computer for determining whether the actual selectivity calculated has reached a selected limit for the selectivity.

Details of block 36 for determining whether the catalyst selectivity has fallen to a set limit, are shown in FIG. 4. This value Z is set in limit unit 38 and is based on manufacturers recommendation and operating experience with the particular catalyst being used.

If the actual selectivity is still above this limit, a signal is supplied over a form message unit 39 to a catalyst status accounting block 40. When actual selectivity has fallen to the limit, a signal is sent to a transfer block 42 for initiating transfer of the process from the primary to the auxiliary reactor.

Figure 5:
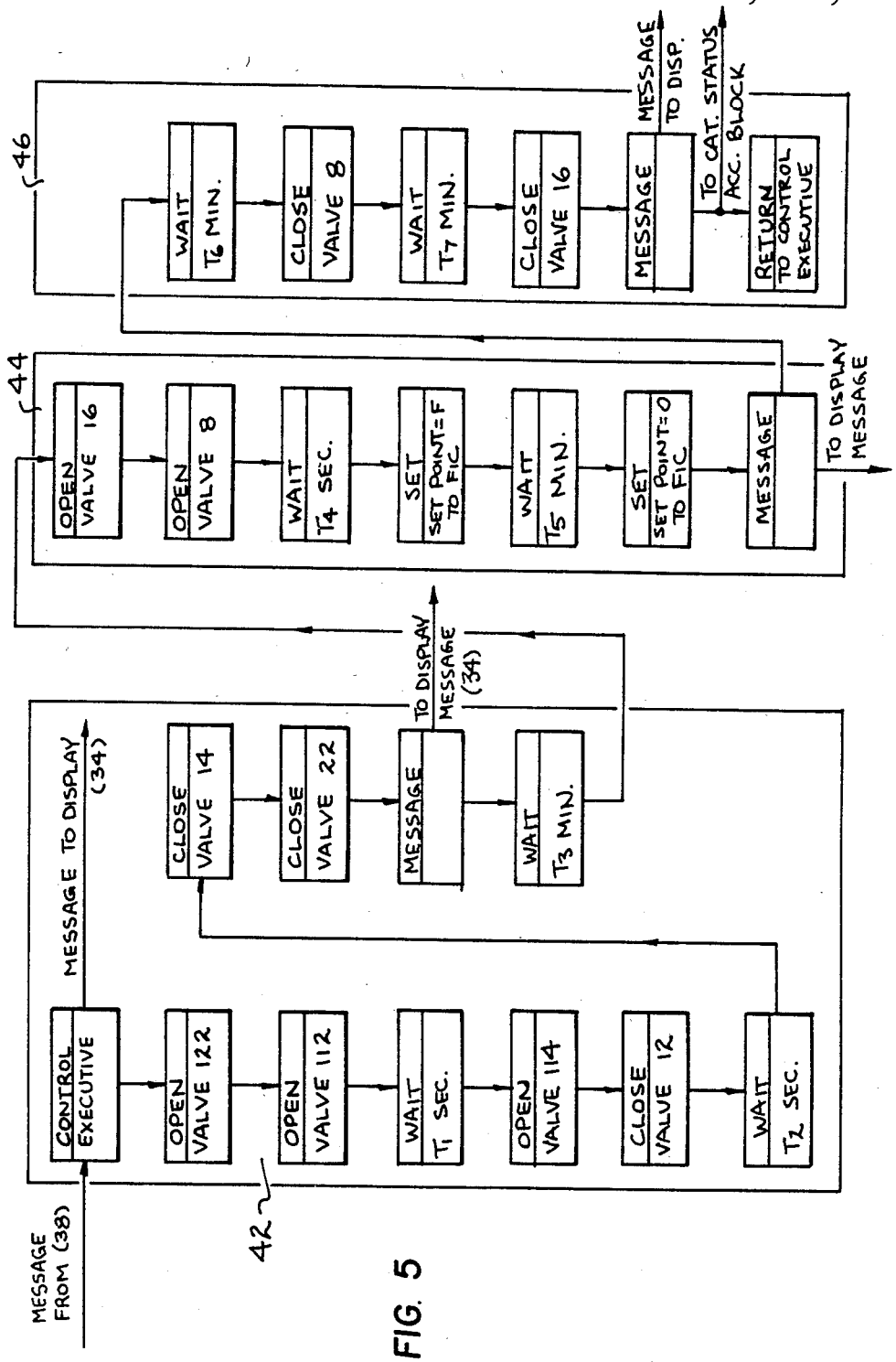
FIG. 5 is a block diagram showing a series of three sub units in the control computer which control the operation of the overall apparatus to transfer operation from one of the reactors to the other reactor and thereafter regenerates the catalyst of the first reactor.

FIG. 5 shows details of the transfer block 42 as well as catalyst regeneration block 44 and ready state block 46.

As shown in FIG. 5, the valves in the apparatus of FIG. 1 are controlled in appropriate sequence and with time delays where necessary.

Valve 122 is first opened to supply coolant to heat exchanger 124 in cooling circuit 118 of auxiliary reactor 110. Valve 112 is then opened to establish a flow of raw materials from feed line 2 to reactor 110. A duration of T1 seconds is then observed to fill reactor 110 on appropriate level, whereafter outlet valve 114 is opened for establishing flow of products to exit line 98. Inlet valve 12 of reactor 10 is then closed and a second time period of T2 seconds is observed. After this time period which permits drainage of primary reactor 10, outlet valve 14 is closed. After this coolant valve 22 is closed and a message is provided to display 34 for the purpose of informing the operator that the initial transfer steps have been taken.

A waiting period of T3 minutes is then observed after which regeneration for primary reactor 10 is commenced. To achieve these control functions, block 44 first opens drain valve 16. Regeneration valve 8 is then opened to commence the regeneration of catalyst in reactor 10. The remainder of steps illustrated in block 44 of FIG. 5 complete the regeneration process in known fashion using the controller 94 and flow transmitter 96 further in conjunction with appropriate programming in control computer system 50.

With regeneration complete, a message signal is again provided to display 34, for operator information. Regeneration valve 8 is then closed by appropriate controls in ready state block 46. After observing an appropriate duration of time T7 for drainage of reactor 10, drain valve 16 is closed and a further message is sent to display 34 which indicates that the primary reactor 10 is now again available for further use. A last step in the automatic regeneration system of the invention is an accounting for the total time between two successive regenerations, the total time for use of catalyst and the total number of regenerations. This is accomplished in control block 40 which is shown in greater detail in FIG. 6.

Figure 6:
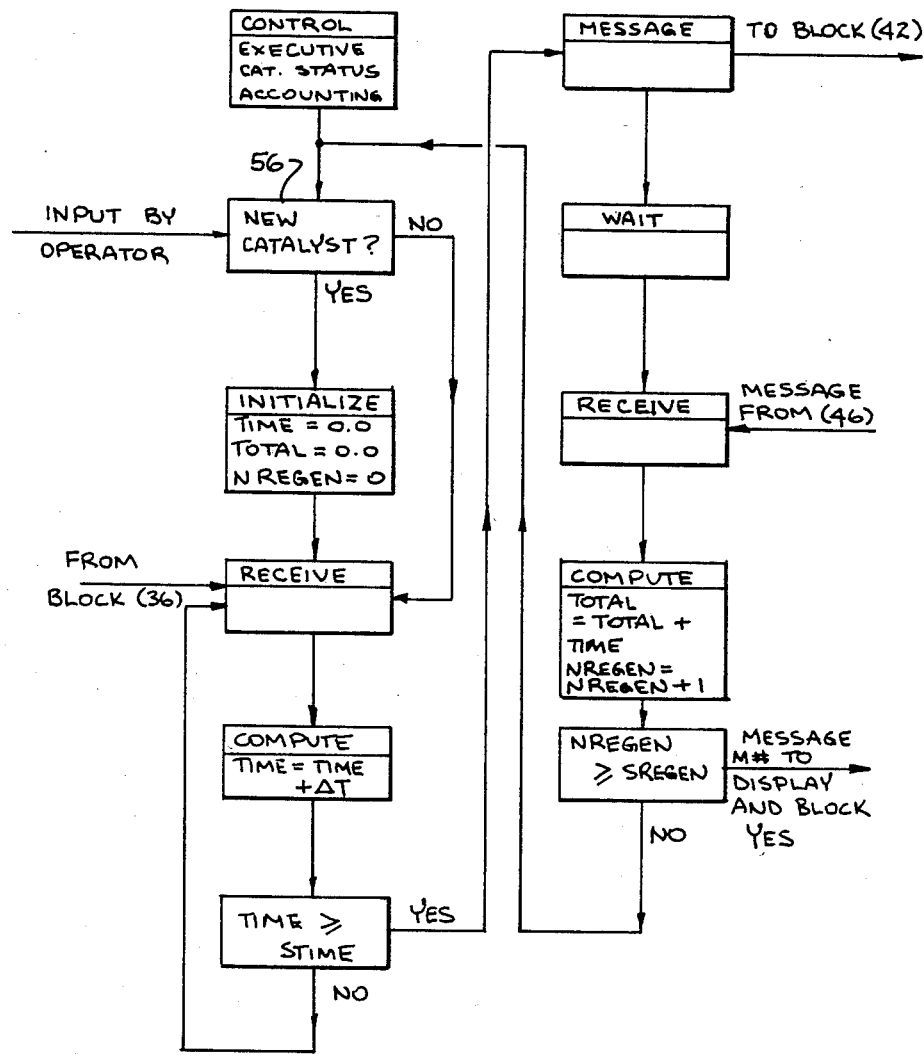
FIG. 6 is a block diagram showing additional details of units in the control computer for monitoring catalyst status and for setting various time durations used in controlling the apparatus using the control elements of FIG. 5.

The circuit of FIG. 6 permits the operator to manually initiate a regeneration step over a block 56. Regeneration also is begun whenever total time between successive regenerations is greater than a specified time TOTALT. Regeneration may also be initiated when total time for usage exceeds a total specified time STIME. The number of regenerations NGEGEN is also counted in the circuitry of FIG. 6 with a new catalyst being provided after a selected number of regeneration cycles SREGEN.

The various messages which are provided to the operator by the various blocks are as follows:
1. Reactor 10 to be switched to reactor 110 automatically;
2. Reactor switchover complete;

3. Catalyst regeneration process started;
4. Catalyst being regenerated in reactor;
5. Catalyst regeneration complete;
6. Reactor being switched because of
   (a) selectivity below acceptable level or;
   (b) operator demand or;
   (c) operating duration at selected limit; and
7. New catalyst required.

While a specific embodiment of the invention has been shown and described in detail to illustrate the application of the principles of the invention, it will be understood that the invention may be embodied otherwise without departing from such principles.

What is claimed is:

1. A method of controlling catalyst regeneration for a hydrogenation process of a hydrocarbon in a reactor, comprising:

sensing the hydrocarbon raw material concentration in a feed stream of the reactor;

sensing the hydrogen concentration in the feed stream;

sensing the hydrocarbon raw material concentration in an exit stream of the reactor;

calculating an estimated catalyst selectivity according to the relationship, $$S = C_{H1}/(C_{A1} - C_{A2})$$

wherein S = catalyst selectivity, $C_{A1}$ = hydrocarbon raw material concentration in the feed stream, $C_{A2}$ = hydrocarbon raw material concentration in the exit stream, and $C_{H1}$ = hydrogen concentration in the feed stream; and regenerating the catalyst of the reactor when the calculated estimated selectivity of the catalyst reaches a selected level.

2. A method according to claim 1, including displaying the calculated catalyst selectivity to an operator of the reactor.

3. A method according to claim 1, including transferring feed of the feed stream to an auxiliary reactor when the first mentioned reactor is being regenerated, the auxiliary reactor having one of regenerated and fresh catalyst.

4. A method according to claim 1 wherein the hydrocarbon is acetylene.

* * * * *